(12) United States Patent
Hartmann et al.

(10) Patent No.: US 8,460,581 B2
(45) Date of Patent: Jun. 11, 2013

(54) IMIDAZOLE DERIVATIVES AND THEIR USE OF DOPANTS FOR DOPING ORGANIC SEMICONDUCTOR MATRIX MATERIAL

(75) Inventors: Horst Hartmann, Dresden (DE); Olaf Zeika, New York, NY (US); Martin Ammann, Dresden (DE); Rene Dathe, Chemnitz (DE)

(73) Assignee: Novaled AG, Dresden (DE)

( * ) Notice: Subject to any disclaimer, the term of this patent is extended or adjusted under 35 U.S.C. 154(b) by 98 days.

(21) Appl. No.: 12/599,487

(22) PCT Filed: May 9, 2008

(86) PCT No.: PCT/EP2008/003792
§ 371 (c)(1),
(2), (4) Date: Nov. 9, 2009

(87) PCT Pub. No.: WO2008/138580
PCT Pub. Date: Nov. 20, 2008

(65) Prior Publication Data
US 2010/0301277 A1    Dec. 2, 2010

(30) Foreign Application Priority Data
May 10, 2007   (EP) ..................... 07009366

(51) Int. Cl.
H01B 1/00    (2006.01)
(52) U.S. Cl.
USPC ......... 252/500; 252/62.2; 252/519.2; 257/40; 548/313.4; 548/343.1
(58) Field of Classification Search
USPC ...... 252/62.2, 500, 519.2; 257/40; 548/343.1, 548/313.4
See application file for complete search history.

(56) References Cited

U.S. PATENT DOCUMENTS

| | | | |
|---|---|---|---|
| 2,566,208 A | 8/1951 | Jenkins | |
| 3,083,242 A | 3/1963 | Ramsden | |
| 3,226,450 A | 12/1965 | Blazejak et al. | |
| 3,558,671 A | 1/1971 | Martin | |
| 3,563,751 A | 2/1971 | Cohen | |
| 4,003,943 A | 1/1977 | Fukunaga | |
| 4,066,569 A | 1/1978 | Lim | |
| 4,133,821 A | 1/1979 | West et al. | |
| 4,618,453 A | 10/1986 | Kim | |
| 4,960,916 A | 10/1990 | Pazik | |
| 5,093,698 A | 3/1992 | Egusa | |
| 5,110,835 A | 5/1992 | Walter et al. | |
| 5,247,226 A | 9/1993 | Sato et al. | |
| 5,281,730 A | 1/1994 | Zambounis et al. | |
| 5,292,881 A | 3/1994 | Berneth et al. | |
| 5,393,614 A | 2/1995 | Nakada | |
| 5,556,524 A | 9/1996 | Albers | |
| 5,811,833 A | 9/1998 | Thompson | |
| 5,840,217 A | 11/1998 | Lupo et al. | |
| 5,922,396 A | 7/1999 | Thompson et al. | |
| 6,013,384 A | 1/2000 | Kido et al. | |
| 6,013,982 A | 1/2000 | Thompson et al. | |
| 6,103,459 A | 8/2000 | Diel et al. | |
| 6,207,835 B1 | 3/2001 | Reiffenrath et al. | |
| 6,350,534 B1 | 2/2002 | Boerner et al. | |
| 6,423,429 B2 | 7/2002 | Kido et al. | |
| 6,524,728 B1 | 2/2003 | Kijima et al. | |
| 6,700,058 B2 | 3/2004 | Nelles et al. | |
| 6,747,287 B1 | 6/2004 | Toguchi et al. | |
| 6,824,890 B2 | 11/2004 | Bazan et al. | |
| 6,908,783 B1 | 6/2005 | Kuehl et al. | |
| 6,972,334 B1 | 12/2005 | Shibanuma et al. | |
| 7,081,550 B2 | 7/2006 | Hosokawa et al. | |
| 7,345,300 B2 | 3/2008 | Qin | |
| 8,134,146 B2 * | 3/2012 | Limmert et al. | ................ 257/40 |
| 2003/0064248 A1 | 4/2003 | Wolk | |
| 2003/0165715 A1 | 9/2003 | Yoon et al. | |
| 2003/0234397 A1 | 12/2003 | Schmid et al. | |
| 2004/0068115 A1 | 4/2004 | Lecloux et al. | |
| 2004/0076853 A1 | 4/2004 | Jarikov et al. | |
| 2005/0040390 A1 | 2/2005 | Pfeiffer et al. | |
| 2005/0061232 A1 | 3/2005 | Werner et al. | |
| 2005/0072971 A1 | 4/2005 | Marrocco et al. | |
| 2005/0086251 A1 | 4/2005 | Hatscher et al. | |
| 2005/0110009 A1 | 5/2005 | Blochwitz-Nimoth et al. | |
| 2005/0121667 A1 | 6/2005 | Kuehl et al. | |
| 2006/0049397 A1 | 3/2006 | Pfeiffer et al. | |
| 2007/0026257 A1 | 2/2007 | Begley et al. | |
| 2007/0058426 A1 | 3/2007 | Sokolik et al. | |
| 2007/0090371 A1 | 4/2007 | Drechsel et al. | |

(Continued)

FOREIGN PATENT DOCUMENTS

| | | |
|---|---|---|
| CA | 2549309 | 9/2005 |
| CH | 354065 | 5/1961 |

(Continued)

OTHER PUBLICATIONS

Akiba, Kin-Ya et al., "Direct Synthesis of 2,2-diaryl-3-methyl-2,3-dihydrobenzothiazoles from 3-methyl-2,3-dihydrobenzothiazole-2-thione and some mechanistic aspects," Bulletin of the Chemical Society of Japan, vol. 52(1), pp. 156-159, (1979).

Akutagawa, T. et al. "Multi Electron and Proton-Transfer System Based on 2,2'-biimidazole derivatives," Science and Technology of Syn. Metals, 1994, 346.

Alonso, R. A. et al. "Photostimulated Reaction of Diphenylarsenide and Diphenylstibide Ions with Haloaromatic Compounds by the Srn1 Mechanism. Electron Transfer vs. Bond Breaking of the Radical Anion Intermediate," J. Org. Chem. (1982) 47(1) pp. 77-80.

(Continued)

Primary Examiner — Khanh Tuan Nguyen
(74) Attorney, Agent, or Firm — Sutherland Asbill & Brennan LLP

(57) ABSTRACT

The present invention relates to imidazole derivatives and their use as dopants for doping an organic semiconductor matrix material, organic semiconductor materials and electronic or optoelectronic structural elements.

6 Claims, No Drawings

U.S. PATENT DOCUMENTS

| | | | |
|---|---|---|---|
| 2007/0116984 A1 | 5/2007 | Park et al. | |
| 2007/0145355 A1 | 6/2007 | Werner et al. | |
| 2007/0252140 A1 | 11/2007 | Limmert et al. | |
| 2008/0103315 A1 | 5/2008 | Egawa et al. | |
| 2008/0122345 A1 | 5/2008 | Sakata et al. | |
| 2008/0145708 A1 | 6/2008 | Heil et al. | |
| 2008/0265216 A1 | 10/2008 | Hartmann et al. | |
| 2009/0001327 A1 | 1/2009 | Werner et al. | |
| 2010/0222598 A1* | 9/2010 | Komatsu et al. | 548/343.1 |

FOREIGN PATENT DOCUMENTS

| | | |
|---|---|---|
| CH | 354066 | 5/1961 |
| DE | 19836408 | 2/2000 |
| DE | 10261662 | 7/2004 |
| EP | 1000998 | 5/2000 |
| JP | 61254582 | 11/1986 |
| JP | 63172274 | 7/1988 |
| JP | 63172275 | 7/1988 |
| JP | 04338760 | 11/1992 |
| JP | 7168377 | 7/1995 |
| JP | 2004010703 | 1/2004 |
| JP | 2004335557 | 11/2004 |
| WO | WO 03/088271 | 10/2003 |
| WO | WO 03/104237 | 12/2003 |
| WO | WO 2006/067800 | 6/2006 |
| WO | WO 2008/022633 | 2/2008 |

OTHER PUBLICATIONS

Auch et al. "Eine neue Synthese und die Kristallstrukturanalyse von., Krokonat-Blau . . . ," Chem. Ber. 120, 1691-1696 (1987), extract, pp. 1691-1693, 6 total pages.

Bach, U. et al. "Solid-state dye-sensitized mesoporous $TiO_2$ solar cells with high photon-to-electron conversion efficiencies," Nature, vol. 395, Oct. 8, 1998, pp. 583-585.

Bamgboye, T.T. et a. "Lewis acidity of Ph2SbX3, wherein X = Cl or Br. Crystal structures of Ph2SbCl3*H20 and Ph2SbBr3*MeCN," J. Of Organometallic Chem. vol. 362, Feb. 28, 1989, pp. 77-85.

Bard, A. J., Faulkner, R.J., Electrochemical Methods: Fundamentals and Applications, Wiley, 2nd Ed., 2000 (Chapter 6).

Barton, D.H.R. et al. "Comparative Arylation Reactions with Pentaphenylbismuth and with Triphenylbismuth Carbonate," J. Chem. Soc. Chem. Commun. (1980) 17, pp. 827-829.

Baumgartel, H. et al., "Polarographische Untersuchungen zur Konformation von 1.2.3.4.5-pentaarylimidazoliumkationen," Ber. Bunsenges (1972) 76/2, 94-100.

Baumgartel, H. et al.,"Uber eine neue Synthese von tetraaryl-imidazolen und pentaaryl-imidazolium-salzen," Chem. Ber. (1968), 101, 3504.

Bhattacharya, S.N. et al. "Preparation & Characterization of Some Triarylarsenic & Triarylantimony Mixed Halides & Related Compounds," Indian J. Chem. 16A (1978) pp. 778-781.

Blinka et al. "Octacyanotetramethylenecyclobutane Dianioin and its Anion-Radical," Tetrahedron Lett. (1983). vol. 24, No. 1567-1568.

Blochwitz, J., et al., "Low voltage organic light emitting diodes featuring doped phthalocyanine as hole transport material," Applied Physics Letters, vol. 73, No. 6, Aug. 10, 1998, pp. 729-731.

Bonati, F. et al. "Reactions of C-imidazolyllithium derivatives with Broup Ib compounds: tris[micro-(1-alkylimidazolato-N3, C2)]tri-gold (I) and -silver (I)," J. Organomet. Chem. 1989, 375, pp. 147-160.

Brucsis, L. et al. "Substituionasreaktionen an 1,4-dihalogen-2,3,5,6-tetracyan-benzolen," Chem. Ber. 109(1976) pp. 2469-2474.

Cherkashin M. I. et al. "Studies on 2,4,5-triarylimidazoles," Izv. Akad. Nauk SSSR, Seriya Khim. 1982, 2, pp. 376-377.

Chonan et al. "The synthesis of difluoro and dimethyl derivatives of 2,6-bis(dicyanomethylene)-2,6-dihydro-4H-cyclopenta[2,1-b:3,4-b']-dithiophen-4-one (CPDT-TCNQ) and the Conducting Properties of the Metallic Salts Based on the Dimethy Derivative," The Chemical Society of Japan (2004) pp. 1487-1497.

Curini, M. et al., "Ytterbium Triflate Promoted Synthesis of Benzimidazole Derivatives," Synlett, No. 10, pp. 1832-1834, 2004.

Dedik, S.G. et al. "Tetrahalotetraazafulvalenes—new strong electron acceptors," Chemistry of Heterocyclic Compounds (A Translation of Khimiyageterotsiklicheskikh Soedinenii), Plenum Press Co., New York, U.S., vol. 10, Jan. 1, 1989, p. 1421.

Deluca, Mark et al., "The p-toluenesulfonic acid promoted synthesis of 2-substituted benzoxazoles and benzimidazoles from diacylated precursors," Tetrahedron, vol. 53, No. 2, pp. 457-464, 1997.

Endo, Jun et al., "Organic Electroluminescent Devices with a vacuum-deposited Lewis Acid doped hole injecting layer," Japan Society of Applied Physics, vol. 41, 2002, pp. L358-L360, Part 2, No. 3B, Mar. 15, 2002.

Fatiadi et al. "Electrochemical Oxidation of Several Oxocarbon Salts in N,N-dimethylformamide," J. Electroanalytical Chem. (1982) vol. 135, pp. 193-209.

Fatiadi, "Psuedooxocarbons, Synthesis of 1,2,3-tris(dicyanomethylene)croconate Salts; A New Bond-Delocalized Dianion, Croconate Blue," J. Org. Chem. 1980, 45, 1338-1339.

Fatiadi, "Synthesis of 1,3-(dicyanomethylene)croconate Salts. New Bond-Delocalized Dianion, Croconate Violet," Journal of the American Chemical Society, Apr. 12, 1978, pp. 2586-2587.

Fausett, B.W. et al. "Palladium-catalyzed coupling of thiol esters with aryl and primary and secondary alkyl organiindium reagents," J. Org. Chem. (2005) 70(12) pp. 4851-4853.

Fenghong Li et al., "Leuco Crystal Violet as a dopant for n-doping of organic thin films of fullerene C60," J. Phys. Chem. B 2004, 108, pp. 17076-17088.

Fild, Manfred et al. "Group VA pentafluorophenyl compounds. 14. Pentafluorophenyl—substituted phosphoranes," Zeitschrift Fuer Anorganische und Allgemeine Chemie, 439, pp. 145-152 (1978).

Fukunaga, T. et al. "Negatively substituted trimethylenecyclopropane dianions," J. Am. Chem. Soc., 1976, pp. 610-613.

Gan, F. "Optical nonlinearity of hybrid and nanocomposite materials prepared by the Sol-Gel method," J. of Sol-Gel Science and Technology, 13, 559-563 (1998).

Ganzorig, C. et al., "p-Typed Semiconducts of Aromatic Diamines Doped with SbC15," Chemistry Letters 2000, pp. 1032-1033.

Gibbons, M.N. et al. "Multiply Bridged Diantimony Compounds," Phosphorus, Sulfur, & Silicon 93/94 (1994).

Giovanella, et al. "Electroluminescence from two fluorinated organic emitters embedded in polyvinyl carbazole," Applied Physics Letters, vol. 87, pp. 171910-1-3.

Glemser, O. et al. "Synthese von Tris-pentafluorphenylarsin, -stibin und -phosphin sowie von Trimethyl-pentafluor-phenylsilan," Angew. Chemie (1964) 76, 953.

Gogoi, P. et al. "An efficient and one-pot synthesis of imidazolines and benzimidazoles via anaerobic oxidation of carbon-nitrogen bonds in water," Tetrahedron Lett. 2006, 47, pp. 79-82.

Gregg, B.A. et al., "On the superlinear increase in conductivity with dopant concentration in excitonic semiconductors," Applied Physics Letters, vol. 84, No. 10, Mar. 8, 2004, pp. 1707-1709.

Grimmett, M. R., "Imidazole and benzimidazole synthesis," Tables of Contents, pp. 1-10, Academic Press, Harcourt Brace & Company, Publishers, London, San Diego, NY, Boston et al., 1997.

Gufeng, He et al., "High-efficiency and low-voltage p-i-n. electrophosphorescent organic light-emitting diodes with double-emission layers," Applied Physics Letters, vol. 85, No. 17, Oct. 25, 2004, pp. 3911-3913.

Haddon, R.C. et al., "Conducting films of C60 and C70 by alkali-metal doping," Nature, vol. 350, Mar. 28, 1991, pp. 320-322.

Harada, Kentaro et al., "Realization of organic pn-homojunction using a novel n-type doping technique, Proceedings of SPIE—The international Society for Optical Engineering; Organic Optoelectronics and Photonics 2004," vol. 5464, Sep. 2004, pp. 1-9.

Harris, G. S. et al."The Reaction of Trispentafluorophenylstibine with Halogens and Interhalogens," J. Fluorine Chem. 37 (1987) pp. 247-252.

Heinze, J. et al., "Polarographic studies of the conformation of 1,2,3,4,5-pentaarylimidazolium cations," the Institute for Physical Chemistry at The University of Freiburg, pp. 1-22, 1972.

Hill, J. "Oxidative Dimerization of Benzimidazole," J. Org. Chem. 1963, 28, pp. 1931-1932.

Hopf et al. "Uber einen neuen Kohlenwasserstoff C18H24 . . . ," Helvetica Chimica Acta, vol. XLIV, Issue II (1961), No. 46, extract from p. 380-386.

Hopf et al., "Preparation and Properties, Reactions, and Applications of Radialenes," Angewandte Chemie, vol. 31, No. 8, Aug. 1992, pp. 931-954.

Iyoda, et al. "Novel synthesis of hexaaryl[3]radialenes via dibromo[3]dendralenes," Tetrahedron Letters 41 (2000), 6 pgs.

Japp, F. et al. "Constitution of Glycosine," J. Chem. Soc. Trans. 1887, 51, pp. 552-557.

Jefferson, Alan M. and Suschitzky, H., "New Route to Nucleophillically Substituted o-phenylenediamines," J.C.S. Chem. Comm. pp. 189-190, 1997.

Jensen, W.B.; The Generalized Lewis Acid Based Concepts, John Wiley & Sons, New York, 1980, pp. 113-195.

Ji, L. et al. "Mono-, di- and tetra-nuclear ruthenium (II) complexes containing 2,2'-p-phenylenebis(imidazo[4,5-f]phenanthroline): synthesis, characterization and third-order non-linear optical properties," J. Chem. Soc., Dalton Trans. 2001, pp. 1920-1926.

Katz, H.E. et al., "Pyridyl Dicyanoquinodimethane Acceptors for Electroactive Solids," J. Org. Chem. 56 (1991) pp. 5318-5324.

Kaufhold, Von Jurgen et al., "Uber das Leitfahigkeitsverhalten verschiedener Phthalocyanine im Vakuum und unter dem Einfluss von gasen," Ber. Bunsen. Phys. Chem. 69, pp. 168-179.

Kikuchi, A et al. "A new family of pi-conjugated delocalized biradicals: electronic structures of 1,4-bis(2,5-diphenylimidazol-4-ylidene)cyclohexa-2,5-diene," J. Phys. Chem. B., 2005, 109, pp. 19448-19453.

Kikuchi, A. et al. "Definitive Evidence for the Contribution of Biradical Character in a Closed-Shell Molecule, Derivative of 1,4-Bis-(4,5-diphenylimidazol-2-ylidene)cyclohexa-2,5-diene," J. Am. Chem. Soc. 2004, 126, pp. 6526-6527.

Kimura, M. et al. "Preparation of 4-(4,5-diphenyl-1H-imidazol-2-yl)benzaldehyde and Its Practical Synthetic Use in the Synthesis of Unsymmetrically Substituted Imidazoles," ITE Letters on Batteries, New Technologies and Medicine, 2002, 3, pp. 30-34.

Klopman, G. "Chemical Reactivity and the Concept of Charge-and Frontier-controlled reactions," Journal of the American Chemical Society., vol. 90, No. 2, Jan. 17, 1968, pp. 223-234.

Koster, et al. "Synthesis and reactions of a tetraquinocyclobutane," Dept. of Chemistry, Univ. of Wisconsin, J. Org. Chem., vol. 40, No. 16, 1975, pp. 2300-2304.

Kozaki, M. et al. "Preparation, Properties, and Reduction of Heteroaromatic Quinoids with 1,4-diazacyclopentadien-2-ylidene Terminals," Org. Lett. 2005, 7, pp. 115-118.

Krebs, F.C. et al. "Superradiant properties of 4,4'-bis(1H-phenanthro[9,10-d]imidazol-2-yl)biphenyl and how a laser dye with exceptional stability can be obtained in only one synthetic step," Tetrahedron Lett. 2001, 42, pp. 6753-6757.

Kulkarni, A.P. et al., "Electron transport materials for organic light-emitting diodes," Chem. Mater. 2004, 16, pp. 4556-4573.

Lane, E.S. "A Modified Benziminazole Synthesis," J. Chem. Soc. 1953, pp. 2238-2240.

Lehmstaedt, K. et al. "Halogen-2,2'-diimidazole and ihre Umsetzungen mit Aminen zu Farbstoffen," Ber. Dt. Chem. Ges. B, 1943, pp. 879-891.

Leyden, R. et al. "Thermally Induced Degradation of 2,3,5,6-tetrachloroterephthalylidenebis(o-aminoaniline)," J. Org. Chem. 1983, 48, pp. 727-731.

Li, J. Y. et al. "Enhancement of green electroluminescence from 2,5-di-p-anisyl-isobenzofuran by double-layer doping strategy," Preparation and Characterization, vol. 446, No. 1, pp. 111-116.

Ludvik, J. and Pragst, F. et al., "Electrochemical generation of triplet states," Journal of Electroanalytical Chemistry, No. 180, pp. 141-156, (1984).

Ludvik, J. and Volke, J. "Evidence for a radical intermediate in the anodic oxidation of reduced nicotinamide adenine dinucleotides obtained by electrogenerated chemiluminescence," Analytica Chimica Acta, 209 (1988) 69-78.

Maennig, B. et al., "Organic p-i-n solar cells," App. Phys. 2004, A 79, pp. 1-14.

Matschke, M. et al. "Bis-4h-imidazoles-tetraazafulvalenes-2,2'-biimidazoles: three variations of one redox system," Tetrahedron, vol. 62, No. 36, Sep. 4, 2006, pp. 8586-8590.

Mayer, U. et al. "Uber 2,3,6,7-tetraphenyl-1,4,5,8-tetraazafulvalen," Tetrahedron Lett. 1966, 42, pp. 5221-5223.

Mayer, U. et al. "Uber Biradikale, Chinone und Semichinone der Imidazolyl-Reihe," Angew. Chem. 1966, 78, p. 303.

Minoura, M. et al. "Hexaaryltellurium, the First Neutral Compounds Comprising Hexaarylated Elements," Angew. Chem. Int. Edit. 35 (22) pp. 2660-2662 (1996).

Miyasato, M. et al. "Syntheses and Reactions of Hexavalent Organitellurium Compounds Bearing Five or Six Tellurium-Carbon Bonds," Chem.-A European J. 10(10) pp. 2590-2600 (2004).

Muramatsu, T. et al, "Visible Light Sensitive Cyclomer and Its Tautomeric Dispiro Compound Formed from Bispyridiny Diradical," J. Am. Chem. Soc. 2005, 127, 4572-3.

Muramatsu, T. et al., "Photosensitive Cyclomer Formation of 1,1'-(1,2-ethanediyl)bis(pyridinyl) diradical and its derivativese," J. Am. Chem. Soc. 1989, 111, 5782-7.

Muramatsu, T. et al., "Preparation and Properties of a novel heterocyclic dispiro compound, 3, 10-diaza-N,N-dimethyldispiro[5.0.5.3]pentadeca-1,4,8,11-tetraene," Chemistry Letters, pp. 151-152, (1996).

Nelsen, Stephen, F.; "Heterocyclic Radical Anions. II. Naphthalic and 1,4,5,8-Naphthalenetetracarboxylic Acid Derivatives," Journal of the American Chemical Society, 89:23, Nov. 8, 1967, pp. 5925-5931.

Oeter, D. et al., "Doping and Stability of Ultrapure alpha-oligothiophene Thin Films," Synthetic Metals, 61, 1993, pp. 147-150.

Okada, K. et al. "Detection of a diradical intermediate in the cis-trans isomerization of 5,5'-bis(4,5-diphenyl-2H-imidazol-2-ylidene)-5,5'-dihydro-delta 2,2'-bithiophene," Tetrahedron Lett. 2006, 47, pp. 5375-5378.

Okada, K. et al. "Novel Dimers of 2,2'-(m-Phenylene)bis(4,5-diphenyl-1-imidazolyl) Diradical," Chem. Lett. 1998, pp. 891-892.

Otero, A. et a. "Pentachlorophenyl-arsenic, -antimony and -bismuth compounds," J. of Organometallic Chemistry, vol. 171, No. 3, Jan. 1, 1979, pp. 333-336.

Otero, A. et al. "Pentafluorophenylantimony compounds," J. Organometallic Chem. 154 (1978) pp. 13-19.

Ouchi, A. et al. "13C-nuclear magnetic resonance of some triaryl- and tri-alkylantimony and -bismuth derivatives," J. of Inorganic and Nuclear Chemistry, vol. 37, Issue 11, Nov. 1975, pp. 2347-2349.

Ouchi, A. et al. "The syntheses and properties of some alkylthioacetato and arylthioacetato derivatives of triphenylantimony(V) and -bismus (V)," J. of Inorganic and Nuclear Chemistry, vol. 37, Issue 12, Dec. 1975, pp. 2559-2561.

Park, S. B. et al. "Highly Efficient, Recyclable Pd(II) Catalysts with Bisimidazole Ligands for the Heck Reaction in Ionic Liquids," Organic Lett. 2003, 5, pp. 3209-3212.

Parthasarathy, G. et al., "Lithium doping of semiconducting organic charge transport materials," J. Appl. Phys., vol. 89, No. 9, May 1, 2001, pp. 4986-4992.

Petzhold, C. "Beitrage zur Synthese funktioneller 1,4,5,8-tetraazafulvalene," Dissertation; Friedrich-Schiller-Universitat Jena; 2006.

Pfeiffer, M, et al., "Doped Organic semiconductors: physics and application in light emitting diodes," Organic Electronics, Elsevier, Amsterdam, NL, vol. 4, No. 2/3, Sep. 2003, pp. 89-103, XP001177135, ISSN: 1556-1199.

Quast, H. and Schmitt, E.; "Note Regarding the Quaternization of Heterocycles," Institute of Organic Chemistry at the University of Wurzburg, Chem. Ber. 101, pp. 4012-4014, (1968).

Rake, A. T. et al. "Pentafluorophenyl and phenyl-phosphinidene ions and their group V analogues," Oms. Organic Mass Spectrometry, vol. 3 Jan. 1, 1970, pp. 237-238.

Rasmussen, P.G. et al. "Complexes of the New Ligand Tetracyanobiimidazole," J. Am. Chem. Soc. 1982, 104, pp. 6155-6156.

Rezende, M. C. et al. "An Alternative Preparation of Bisbenzimidazoles," Syn. Comm. 2001, 31, pp. 607-613.

Rezende, M. et al. "Puzzling Formation of Bisimidazole Derivatives from Hexachloroacetone and Diamines," Tetrahedron Lett. 1996, 37, 5265-5268.

Sakaino, Y. "Structures and Chromotropic Properties of 1,4-bis(4,5-diphenylimidazol-2-yl)benzene Derivatives," J. Org. Chem. 1979, 44, pp. 1241-1244.

Sato, S. et al. "Isolation and Molecular Structure of the Organopersulfuranes [12-S-6(C6)]," J. Am. Chem. Soc. 128(21) pp. 6778-6779 (2006).

Schmidt, "Reaktionen von Quadratsaure and Quadratsaure-Derivaten," Synthesis, Dec. 1980, extract pp. 966, 24 total pages.

Schneiders, P. et al. "Notiz zur Darstellung von 4,4',5,5'-tetrasubstituierten Di-2-imidazolyl-derivaten. Ausgangsprodukte zur Darstellung von 1,4,5,8-tetraazafulvalenen," Chem. Ber. 1973, 106, pp. 2415-2417.

Schwarz, W. M. et al., "Formation of Stable Free Radicals on Electroreduction of N-alkylpyridium salts," J. Am. Chem. Soc., 33 3164 (1961).

Seitz, G., Nachr. Chem. Tech. Lab 28 (1980), No. 11, extract pp. 804-807, total pages. 6: "Pseudooxokohlenstoffe."

Sekine, T. et al. "Dimerizations of pi-Rich N-heteroaromatic compounds and xanthine derivatives," Chem. Pharm. Bull. 1989, 37, pp. 1987-1989.

Sharma, G.D. et al., "Influence of Iodine on the Electrical and Photoelectrical Properties of Zinc Phthalocyanine Think Film Devices," Materials Science and Engineering, B41, 1996, pp. 222-227.

Singhal, K. et al. "One the Lewis acidity of tris(pentafluorophenyl)antimony (V) dichloride towards neutral monodentate O, N and S donor ligands," Journal of Fluorine Chemistry, vol. 121, No. 2, Jun. 1, 2003, pp. 131-134.

Smith, M.B. Organic Synthesis, McGraw-Hill, Inc. 1994, Chapter 1.

Sprenger, et al. "The cyclobutenediylium cation, a novel chromophore from squaric acid," Angew. Chem. International Edition, vol. 6 (1967), No. 6, pp. 553-554.

Suschitzky, H. "Syntheses and Reactions of 2,2'-bisbenzimidazole Systems," J. Heterocyclic Chem. 1999, 36, pp. 1001-1012.

Suzuki, T. et al., "4,7-bis(dimethylamino)benzimidazoles and twin-type derivatives: reversible two-stage redox system modulated by proton-transfer," Tetrahedron Lett. 2003, 44, pp. 7881-7884.

Takahashi et al. "Novel Electron Acceptors for Organic Condcutors: 1,2-Bis(p-benzoquino)-3-[2-(dicyanomethylene)-2,5-thienoquino]cyclopropane Derivatives," J. Chem. Soc., Chem. Commun., 1994, pp. 519-520.

Takahashi et al. "Novel metallic charge-transfer complexes composed of a [3]radialene type acceptor: a 1,2-bis(p-benzoquino)-3-[2-(dicyanomethylene) . . . " Advanced Materials, July No. 7, 3 pgs.

Vaid T.P. et al, "Investigations of the 9,10-diphenylacridyl radical as an isostructural dopant for the molecular semiconductor 9, 10-diphenylanthracene," Chemistry of Materials, American Chemical Society, Bd. 15, Nr. 22, 4292-4299 (2003).

Vyas, P.C. et al. "A simple synthesis of 2,2'-bis-benzimidazoles," Chem. Industry, 1980, pp. 287-288.

Weiss, M. "Acetic Acid-Ammonium Acetate Reactions. 2-Isoimidazoles as Intermediates in Imidazole Formation," J. Am. Chem. Soc. 1952, 74, pp. 5193-5195.

West, R. et al., "Diquinocyclopropanones, Diquinoethylenes, and the Anion-Radical and Free-Radical Intermediates in their Formation," Dept. of Chemistry, Univ. of Wisconsin, Feb. 24, 1975, pp. 2295-2299.

Wintgens, V. et al., "Reduction of Pyrylium Salts: Study by ESR and UV_Visible Spectroscopy of the Reversible Dimerization of the Pyranyl Radical," New. J. Chem., 10/6, 345-350 (1986).

Yamaguchi, et al., "New Approaches to Tetracyanoquinodimethane," Bull. Chem. Soc. Jpn. 62 (1989) pp. 3036-3037.

Yamamoto, Y. et al. "The Electrical Properties of the Poly(N-vinyl Carbazole)-Antimony (V) Chloride (or Iodine) Charge Transfer Complexes," Bull. Chem. Soc. Jap. 1965, 38, 2015-2017.

Yoshiko, S., et al. "The Quinoid-biradical Tautomerism of 3,6-bis(4,5-diphenyl-2-Himidazol-2-ylidene)-1,4-cyclohexadiene," Nippon Kagaku Kaishi, 1972, 1, pp. 100-103.

Yukihiko, T., et al. "Studies on Aromatic Nitro Compounds. V. A Simple One-Pot Preparation of o-Aminoaroylnitriles from Some Aromatic Nitro Compounds," Chem. Pharm. Bull., 33 (4) 1360-1366 (1985).

Zhou, X et al., "Enhanced hole Injection Into Amorphous Hole-Transport Layers of Organic Light-Emitting Diodes Using Controlled p-Type Doping," Adv. Funct. Mater., 2001, 11, No. 4, pp. 310-314.

Ziegenbein, W. "The cyclobutenediylium cation, a novel chromophore from squaric acid," Angew. Chem., 79:12, pp. 581-582 (1967).

English Translation of Japanese Office Action; Japanese Patent Application No. 2005-228491; Apr. 17, 2009.

International Search Report, International App. No. PCT/EP2007/002359, May 24, 2007.

Final Office Action, U.S. Appl. No. 11/688,777; Nov. 27, 2009.

Non-Final Office Action, U.S. Appl. No. 11/688,777; Feb. 2, 2009.

Response to Office Action, U.S. Appl. No. 11/688,777; Sep. 4, 2009.

Response to Office Action, U.S. Appl. No. 11/688,777; Aug. 3, 2009.

Restriction Requirement, U.S. Appl. No. 11/688,777; Mar. 5, 2010.

Response to Restriction Requirement, U.S. Appl. No. 11/688,777; Apr. 1, 2010.

Notice of Allowance, U.S. Appl. No. 11/196,491; Apr. 13, 2009.

Notice of Allowance, U.S. Appl. No. 11/196,491; Oct. 20, 2008.

Response to Office Action for U.S. Appl. No. 11/196,491; Aug. 11, 2008.

Final Office Action, U.S. Appl. No. 11/196,491; Feb. 11, 2008.

Response to Office Action for U.S. Appl. No. 11/196,491; Nov. 5, 2008.

Non-Final Office Action, U.S. Appl. No. 11/196,491, Jul. 3, 2007.

International Search Report and Preliminary Report on Patentability for PCT/DE2008/001080; Jul. 11, 2008.

International Search Report for PCT/DE2008/00654; Jun. 15, 2009.

International Search Report and Preliminary Report on Patentability for PCT/EP2006/010816; Feb. 9, 2007.

Advisory Action for U.S. Appl. No. 11/315,072 mailed Mar. 8, 2010.

Response to Final Office Action for U.S. Appl. No. 11/315,072; Feb. 17, 2010.

Final Rejection for U.S. Appl. No. 11/315,072; Nov. 16, 2009.

Response to Office Action for U.S. Appl. No. 11/315,072; Jul. 29, 2009.

Non-Final Rejection for U.S. Appl. No. 11/315,072; Apr. 29, 2009.

Non-Final Rejection for U.S. Appl. No. 11/315,072; Nov. 12, 2008.

Response to Office Action for U.S. Appl. No. 11/315,072; Feb. 10, 2009.

European Search Report for EP 07009366; Oct. 19, 2007.

International Search Report for PCT/EP2008/003792; Sep. 2, 2008.

Anderson, J.D. et al., "Electrochemistry and Electrogenerated Chemiluminescence Processes of the Componenets of Aluminum Quinolate/Triarylamine, and Related Organic Light emitting Diodes," J. Am. Chem. Soc., 1998, 120, pp. 9646-9655.

Bard, A. J., Faulkner, R.J., Electrochemical Methods: Fundamentals and Applications, Wiley, 2nd Ed., 2000 (Chapter 2).

D'Andrade, B.W. et al., "Relationship between the ionization and oxidation potentials of molecular organic semiconductors," Organic Electronics 6, 2005, pp. 11-20.

Harada, K. et al. "Organic Homojunction Diodes with a High Built-in Potential: Interpretation of the Current-Voltage Characteristics by a Generalized Einstein Relation," Phys. Rev. Lett. 94, 036601 (2005).

Huang, Jingsong et al., "Low-voltage organic electroluminescent devices using pin structures," Applied Physics Letters, vol. 80, No. 1, Jan. 7, 2002, pp. 139-141.

Maitrot, M. et al., "Molecular material based junctions: Formation of a Schottky Contact with Metallophthalocyanine Thin Films Doped by the Cosublimation Method," J. Applied Physics, 60(7), Oct. 1, 1986, pp. 2396-2400.

Miller, L.L. et al., "A simple comprehensive correlation of organic oxidation and ionization potentials," J. Org. Chem., 1972, vol. 37, No. 6, pp. 916-918.

Nollau, A. et al., "Controlled n-type doping of a molecular organic semiconductor: naphthalenetetracarboxylic dianhydride (NTCDA) doped with bis(ethylenedithio)-tetrathiafulvalene (BEDT-TTF)," J. Appl. Phys., vol. 87, No. 9, May 1, 2006, pp. 4340-4343.

Parker, "On the Problem of Assigning Values to Energy Changes of Electrode Reactions," Journal of the American Chemical Society, 96:17, Aug. 21, 1974, pp. 5656-5661.

Pfeiffer, M. et al., "Controlled doping of phthalocyanine layers by cosublimation with acceptor molecules: A systematic Seebeck and conductivity study," Applied Physics Letters, vol. 73, No. 22 Nov. 20, 1998, pp. 3202-3204.

R. Schlaf et al., "Homo/Lumo Alignment at PTCDA/ZnPc and PTCDA/ClInPc Heterointerfaces Determined by Combined UPS and XPS Measurements," J. Phys. Chem. B 1999, 103, pp. 2984-2992.

Tang, C.W. et al., "Organic electroluminescent diodes," Applied Physics Letters, vol. 51, No. 12, Sep. 21, 1987, pp. 913-915.

Tang, T.B. et al., "Ionization thresholds of merocyanine dyes in the solid state," Journal of Applied Physics, vol. 59, (1), Jan. 1986, pp. 5-10.

Werner, A. G. et al., "Pyronin B as a donor for n-type doping of organic thin films," Applied Physics Letters, vol. 82, No. 25, Jun. 23, 2003, pp. 4495-4497.

Yao, Fu et al., "Quantum-chemical predictions of Absolute standard redox potentials of diverse organic molecules and free radicals in acetonitrile," J. Am. Chem. Soc. 2005, 127, pp. 7227-7234.

Zhou, X. et al., "Very low operating voltage organic light-emitting diodes using a p-doped amorphous hole injection layer," Applied Physics Letters, vol. 78, No. 4, Jan. 22, 2001, pp. 410-412.

Zimmerman, T. et al. "Benzocycloalkenone und dihydro-2H, 7H-1-benzopyranone aus 2,4,6-triaryl-pyryliumsalzen und cycloalkan-1,2-dionen," J. Prakt. Chem. 331 pp. 306-318 (1989).

Non-Final Rejection for U.S. Appl. No. 12/046,620; Nov. 25, 2009.

Response to Restriction Requirement for U.S. Appl. No. 12/046,620; Aug. 24, 2009.

Restriction Requirement for U.S. Appl. No. 12/046,620; Jul. 22, 2009.

Disclosure Under 37 C.F.R. § 1.56 for U.S. Appl. No. 12/599,487 Submitted Herewith.

Gao, W. et al., "Effect of electrical doping on molecular level alignment at organic-organic heterojunctions," Applied Physics Letters, vol. 82, No. 26, Jun. 30, 2003, pp. 4815-4817.

Kido, Junji et al., "Bright Organic Electroluminescent Devices Having a Metal-doped Electron-injecting Layer," Applied Physics Letters, vol. 73, No. 20, Nov. 16, 1998, pp. 2866-2868.

* cited by examiner

IMIDAZOLE DERIVATIVES AND THEIR USE OF DOPANTS FOR DOPING ORGANIC SEMICONDUCTOR MATRIX MATERIAL

CROSS-REFERENCE TO RELATED APPLICATION

This is a submission pursuant to 35 U.S.C. 154(d)(4) to enter the national stage under 35 U.S.C. 371 for PCT/EP2008/003792 filed May 9, 2008. Priority is claimed under 35 U.S.C, 119(a) and 35 U.S.C. 365(b) to European Patent Application Number 07009366.1 filed May 10, 2007. The subject matters of PCT/EP2008/003792 and European Patent Application Number 07009366.1 are hereby expressly incorporated herein by reference in their entirety.

The present invention relates to imidazole derivatives and their use as dopants for doping an organic semiconductor matrix material, as a charge injection layer, a matrix material itself, as electrode material or as storage material in electronic or optoelectronic structural elements.

Modifying the electrical properties, more particularly the electrical conductivity of organic semiconductors through doping is known, as is also the case for inorganic semiconductors such as silicon semiconductors. Here, through producing charge carriers in the matrix material an increase in the initially very low conductivity, as well as, depending on the type of dopant used, a change in the Fermi level of the semiconductor is achieved. Doping results in an increase in the conductivity of charge transporting layers, whereby ohmic losses are reduced, and to an improved charge carrier transition between contacts and the organic layer if this organic layer is located between two electrical contacts of opposite polarity. Inorganic dopants, e.g. Lewis acids as electron acceptors (e.g. $FeCl_3$; $SbCl_5$) are usually disadvantageous in organic matrix materials due to their high diffusion coefficients, as they impair the function and stability of the electronic structural elements (1). Outer, Ch. Ziegler, W. Göpel *Synthetic Metals* 1993, 61, 147-50; Y. Yamamoto, S. Kanda, S. Kusabayashi, T. Nogaito, K. Ito, 11. Mikawa, *Bull. Chem Soc. Jap.* 1965, 38, 2015-17; J. Kido et al., *Jpn J. Appl. Phys.* 2002, 41, 358-60). Furthermore the latter dopants exhibit such a high vapour pressure that a technical use in known processing installations for organic electronic components is very questionable. Also, the reduction potentials of these compounds are often too low to dope technically really interesting matrix materials. In addition, the extremely aggressive chemical reaction behaviour of these dopants makes a technical application difficult.

The object of the present invention is to overcome the disadvantages of the state of the art. More particularly imidazole derivatives are to be provided that result in improved organic semiconductor matrix materials, charge injection layers, electrode materials, matrix materials themselves or storage material, more particularly when used in electronic and optoelectronic structural elements. The imidazole derivatives used should exhibit sufficiently high reduction potentials without being disturbing influences on the matrix material and provide an effective increase in the charge carrier number in the matrix material and be comparatively simple to use in the sense of use in the processing of electronic components.

Further objects of the invention lie in the provision of organic semiconductor materials and electronic structural elements or optoelectronic structural elements in which the disclosed compounds can be used.

The first object is achieved by the imidazole derivatives according to the following formulae:

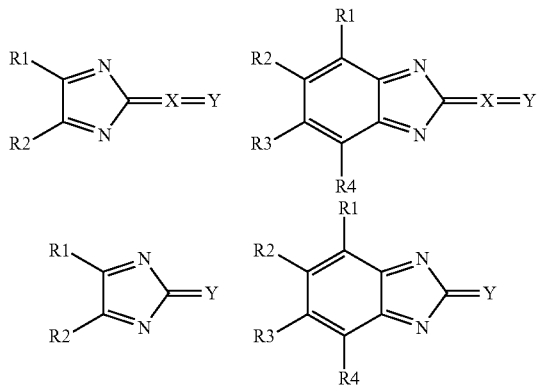

whereby X is selected from substituted and non-substituted, conjugated double-bond systems, substituted and non-substituted, quinoid aromatic and quinoid anellated aromatic ring systems, substituted and non-substituted, quinoid heteroaromatic and quinoid anellated heteroaromatic ring systems; Y is selected from 2-indandione derivatives, $C(CN)_2$, NCN, O, 2-cyclopentadiene derivatives, 2-cyclopentenedione derivatives, $C(CF_3)_2$, C(CN)aryl, C(CN)oligoalyl, C(CN)heteroaryl, $C(CF_3)$aryl; $C(CF_3)$oligoaryl, $C(CF_3)$heteroaryl, N-aryl, N-heteroaryl, N-oligoaryl, acceptor-substituted aryl and acceptor-substituted heteroaryl with more than six ring atoms; $R_1$-$R_4$ are independently selected from the group consisting of hydrogen, substituted and unsubstituted aryls, substituted and unsubstituted heteroaryls, substituted and unsubstituted conjugated hydrocarbon chains with alternating C—C single and double bonds, halogen, cyano, pseudohalogen, nitro, halogenated and perhalogenated alkyls, carboxylic acids and derivatives thereof, sulphonic acids and derivatives thereof, wherein at least one of $R_1$-$R_4$ is no hydrogen, or wherein two adjacent $R_1$-$R_4$ are element of an aromatic ring system anellated to the imidazole ring. Further objects are achieved by the use of the imidazole derivatives as dopants for doping an organic semiconductor matrix material, as a charge injection layer, as matrix material itself, as electrode material or as storage material in electronic or optoelectronic structural elements; organic semiconductor materials comprising at least one organic matrix compound and one dopant, characterised in that one of the imidazole derivatives is used as the dopant; and electronic and optoelectronic structural elements with an electronically functional area, characterised in that for the electronically active area at least one of the imidazole derivatives is used.

Surprisingly it was found that when using the disclosed imidazole in accordance with the invention a much stronger and/or stable p-dopant is present than in previously known donor compounds.

More particularly the conductivity of charge transporting layers when used in accordance with the invention is considerably increased and/or the transition of the charge carriers between the contacts and the organic layer is considerably improved in applications as an electronic component. Without being restricted to what has been set out, it is assumed that when the imidazole derivatives are used in accordance with the invention CT complexes are formed in a doped layer, particularly through the transfer of at least one electron from the surrounding matrix material to the dopant. During the course of this cations of the matrix material are formed which are mobile on the matrix material. In this way the matrix material acquires a conductivity that is increased compared with the conductivity of the undoped matrix material. Conductivities of undoped matrix materials are generally <$10^{-8}$ S/cm, particularly frequently <$10^{-10}$ S/cm. It should be ensured that the matrix materials exhibit a sufficiently high degree of purity. Such levels of purity can be achieved with conventional methods, for example, gradient sublimation. Doping allows the conductivity of such matrix materials to increase to more than $10^{-8}$ S/cm, often >$10^{-5}$ S/cm. This applies in particular to matrix materials exhibiting an oxidation potential of greater than −0.5 V vs. Fc/Fc$^+$, preferably greater than 0 V vs. Fc/Fc$^+$, more particularly greater than +0.2 V vs. Fc/Fc$^+$. The term Fc/Fc$^+$ refers to the redox pair ferrocene/ferrocenium, which is used as the reference when determining electrochemical potential, for example cyclovoltametry.

In accordance with the invention it was also found that the described imidazole derivatives can also be used as an injection layer in electronic components, preferably between an electrode and a semiconductor layer, that can also be doped, or as a blocker layer, preferably between the emitter and transport layer in electronic structural elements. The dopants described in this invention exhibit a surprisingly high stability with regard to their reactivity with the atmosphere.

In addition to the described quinoid form, the imidazole derivatives used as dopants can also be of a pronounced biradical or dipolar ionic nature in their most stable structure (A. Kikuchi, H. Ito, Abe, *J. Phys. Chem. B* 2005, 109, 19448-19453; A. Kikuchi, F. Iwahori, J. Abe, *Am. Chem. Soc.* 2004, 126, 6526-6527; T. Suzuki, et. al., *Tetrahedron Lett.* 2003, 44, 7881-7884; K. Okada et al., *Chem. Lett.* 1998, 891-892; M. Kozaki, A. Isoyama, K. Okada, *Tetrahedron Lett.* 2006, 47, 5375-5378; S. Yoshiko et al., *Nippon Kagaku Kaishi*. 1972, 1, 100-3). Derivatives of the imidazole derivatives described here have already been used in fluorescence dyes (R. Beckert et al., DE 10261662), as photosensitisers in photodynamic therapy (B. Bilbao et al., WO 2003104237) as well as in the form of precursors for the chemical vacuum deposition of materials for organic electronic components (D. Bruce, WO 2000053613) and in electrophotographic applications as materials for photoconductive layers (F. Katsunori, JP 63172274).

The described electron-accepting imidazole derivatives can also be used as a hole injection layer. Thus, for example an anode/acceptor/hole transporter layer structure can be produced. Here the hole transporter can be a pure layer or a mixed layer. More particularly, the hole transporter can also be doped with an acceptor. The anode can, for example, be ITO. The acceptor layer can, for example, be 0.5-100 nm thick.

Preparation of Asymmetric Quinoid Imidazole Derivatives

To produce an imidazole derivative with structure (4), in accordance with the chemical equation shown below, compound 1 can, for example, be condensed with dithioacetal in order to produce type 3 2-hydroimidazoylilidene, see II Farmaco 56 (2001), 277-283. The reaction is carried out in ethanol under reflux. Compound 2 is commercially available.

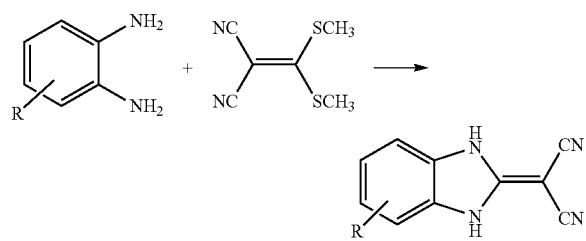

Due to the electron-deficient nature of the (CN)$_2$C group compound 3 can then be deprotonated, and in the presence of an oxidation agent is converted to the type 4 p-dopant (strong acceptors).

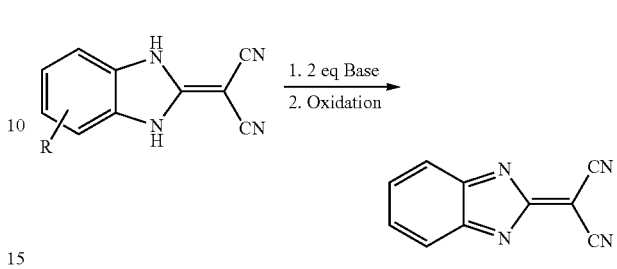

Preparation of Symmetric Quinoid Bisimidazole Derivatives

The described imidazole derivatives can be synthesised in accordance with known methods. Preparation starts with the provision of benzoid bisimidazoles that are converted into their anions and through suitable oxidation agents converted into the quinoid bisimidazole in accordance with the following general diagram:

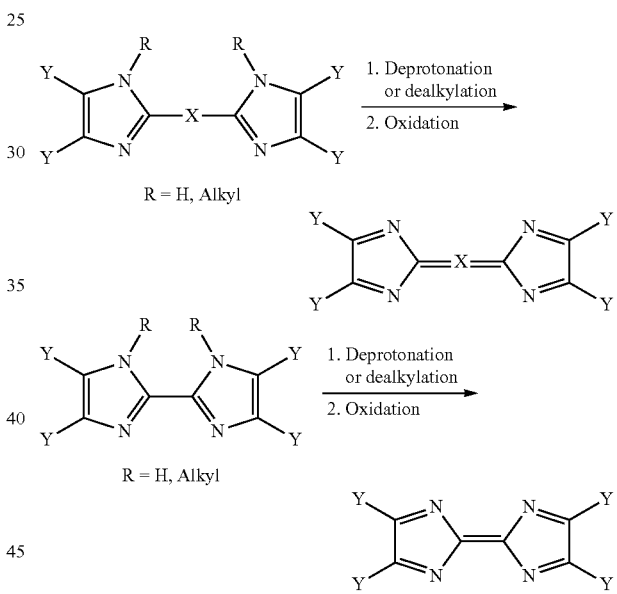

Here oxidation can also take place without prior deprotonation directly from the benzoid bisimidazole form or from a precursor state with substitution of the N atoms (R=any branched or unbranched alkyl residue or substituted alkyl residue). Examples of the preparation of the initially required materials, the aryl-bridged benzoid bisimidazoles (X=aryl or heteroaryl), are described in detail in the literature and are based, for example, on the condensation of diketones with aryl or heteroaryl carbodialdehydes (M. Weiss, *J. Am. Chem., Soc.* 1952, 74, 5193-5195; U. Mayer, H. Baumgärtel, H. Zimmermann, *Tetrahedron Lett.* 1966, 42, 5221-5223; P. Schneiders, J. Heinze, H. Baumgärtel, *Chem. Ber.* 1973, 106, 2415-2417; M. Kozaki, A. Isoyama, K. Akita, K. Okada, *Org. Lett.* 2005, 7, 115-118; Ji, X.-Y. Li et al., *J. Chem. Soc., Dalton Trans.* 2001, 1920-1926; F. C. Krebs et al., *Tetrahedron Lett.* 2001, 42, 6753-6757). Asymmetrical derivatives of aryl-bridged benzoid bisimidazoles are Also accessible in this way (M. Kimura et al., *ITE Letters on Batteries, New Technologies and Medicine* 2002, 3, 30-34). Another method or producing bisimidazoles is the condensation of diamines with carbodialdehydes with subsequent oxidative cyclisation of the formed diimine (R. Leyden et al. *J. Org. Chem.* 1983, 48, 727-731; P. Gogoi, D. Konwar, *Tetrahedron Lett.* 2006, 47, 79-82). Bisimidazoles can also be produced through the condensation of diamines with oxalic acid derivatives or with appropriate diacarboxylic acids (E. S. Lane, *J. Chem. Soc.* 1953, 2238-2240; H. Suschitzky, *J. Heterocyclic Chem.* 1999, 36, 1001-1012; J. Hill, *J. Org. Chem.* 1963, 28, 1931-2; P. C. Vyas, C. Oza, A. K. Goyal, *Chem. Industry* 1980, 287-288) or through the condensation of diketones with glyoxal (F. Japp, E. Cleminshaw, *J. Chem. Soc. Trans.* 1887, 51, 552-557) or through the conversion of phenylene diamines with hexachloroacetone Rezende, E. L. Dall'Oglio, C. Zucco, *Syn. Comm.* 2001, 31, 607-613; M. Rezende, H. C. Zucco, *Tetrahedron Lett* 1996, 37, 5265-5268;). Syntheses of bisimidazoles can also take place through the catalytic dimerisation of imidazoles or benzimidazoles or their N-alkylated derivatives (T. Sekine et al., *Chem. Pharm. Bull.* 1989, 37, 1987-1989) or by way of metal-organic, generally copper-mediated bonding of 2 metallised imidazoles or benzimidazoles (S. B. Park, H. Alper, *Organic Lett.* 2003, 5, 3209-3212; F. Bonati, A. Burini, B. R. Pietroni, *J. Organomet. Chem.* 1989, 375, 147-160) or through ring bonding between an imidazole and a 2-diazoimidazole (P. G. Rasmussen et al., *J. Am. Chem. Soc.* 1982, 104, 6155-6156).

The direct oxidation of benzoid bisimidazoles to form the actual dopants, the quinoid bisimidazoles, through commonly used oxidation agents such as manganese dioxide or lead (IV) acetate is known (U. Mayer, H. Baumgärtel, H. Zimmermann, *Tetrahedron Lett.* 1966, 42, 5221-5223; H. Suschitzky, *J. Heterocyclic Chem.* 1999, 36, 1001-1012; J. Hill, *J. Org. Chem.* 1963, 28, 1931-1932) and can also take place directly from the benzoid bisimidazoles in a 2 phase mixture of the organic solution of the benzoid precursors with the oxidation agent, e.g. potassium ferricyanide in a alkaline aqueous solution (M. Kozaki. A. Isoyama, K. Akita, K. Okada, *Org. Lett.* 2005, 7, 115-118; K. Okada et al., *Chem. Lett.* 1998, 891-892; Cherkashin M. I. et al. *Izv. Akad. Nauk SSSR. Seriya Khan.* 1982, 2, 376-377) or through oxidation of the silver salt or the sodium salt of the benzoid bisimidazoles with bromine in organic solvents (U. Mayer, Baumgärtel, H. Zimmermann, *Angew. Chem.* 1966, 78, 303; S. Dedik et al. *Khimiya Get. Soed.* 1989, 10, 1421).

The quinoid bisimidazoles used as dopants can also be produced through the photochemical excitation of suitable precursors, for example in UV irradiation (Y. Sakaino, *J. Org. Chem.* 1979, 44, 1241-1244). These precursors are generally alkoxy adducts of the quinoid bisimidazoles which in turn are available through the addition of alcohols in the base-catalysed oxidation of the benzoid bisimidazoles to quinoid bisimidazoles.

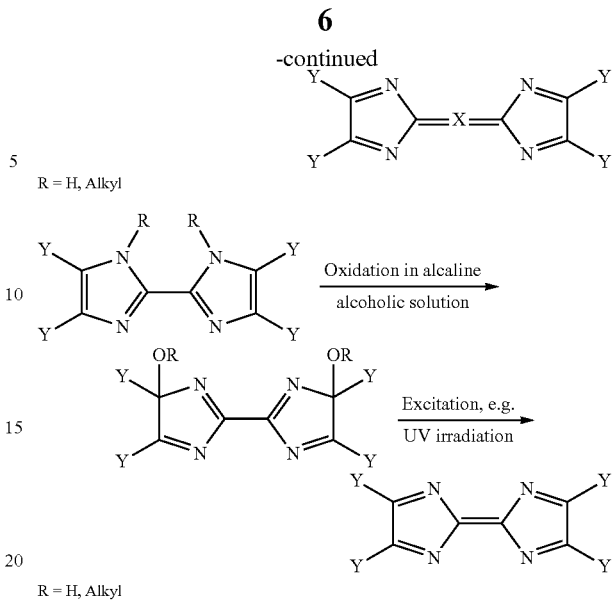

EXAMPLES OF EMBODIMENT OF THE SYNTHESIS OF SYMMETRIC QUINOID BISIMIDAZOLS

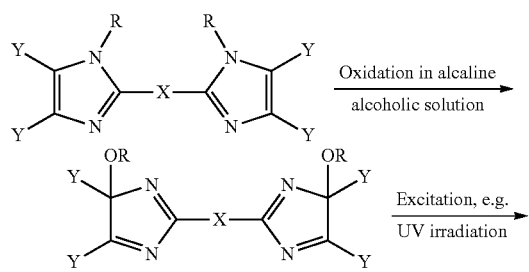

The tetrabromide imidazol B was produced by way of bromination of commercially available bisimidazole A in a modification of known specifications (K. Lehmstaedt, H. Rolker, *Ber. Dt. Chem. Ges. B* 1943, 879-891): 520 mg (3.88 mmol) bisimidazole and 2.13 g (15.7 mmol) sodium acetate trihydrate are placed in 10 ml glacial acetic acid and a solution of 2.48 g (15.5 mmol) bromine in 10 mL glacial acetic acid is added drop by drop. After completed addition, heating to 100° C. takes place for 2 hours. The preparation is evaporated to dry and boiled off with diluted hydrochloric acid, extracted while hot, rinsed with diluted HCl and water and dried. Yield 1.11 g B (64% d.Th). HPLC analysis of the product resulted in a purity of 90%, DI-MS m/z=450, the isotope pattern corresponds to 4 bromine substitutes.

The preparation of the quinoid dopant C took place in accordance with a modification of a known specification (S. Dedik et al. *Khimiya Get. Soed.* 1989, 10, 1421) through heating 565 mg (1.26 mmol) tetrabromide diimidazol B with 428 mg (2.52 mmol) silver nitrate in 40 ml absolute EtOH for 1 hour under reflux and extraction of the formed product. This product was suspended in 20 mL absolute dichloromethane, cooled to 0° C. and mixed with 12.8 mL 0.1 M bromine in dichloromethane. The preparation was stirred for 15 minutes during cooling and for 30 minutes at room temperature, extracted from the salts, rinsed with dichloromethane and the combined filtrates evaporated. Raw yield 418 mg (74% d.Th.). DI-MS (EI): m/z=448. Before being tested as a dopant the raw product underwent gradient sublimation at 160-170° C. and approx. $10^{-4}$ mbar. In a cyclovoltametric analysis the sublimated product showed a first reduction potential of −0.24 V vis-à-vis Fc/Fc$^+$.

Example 2

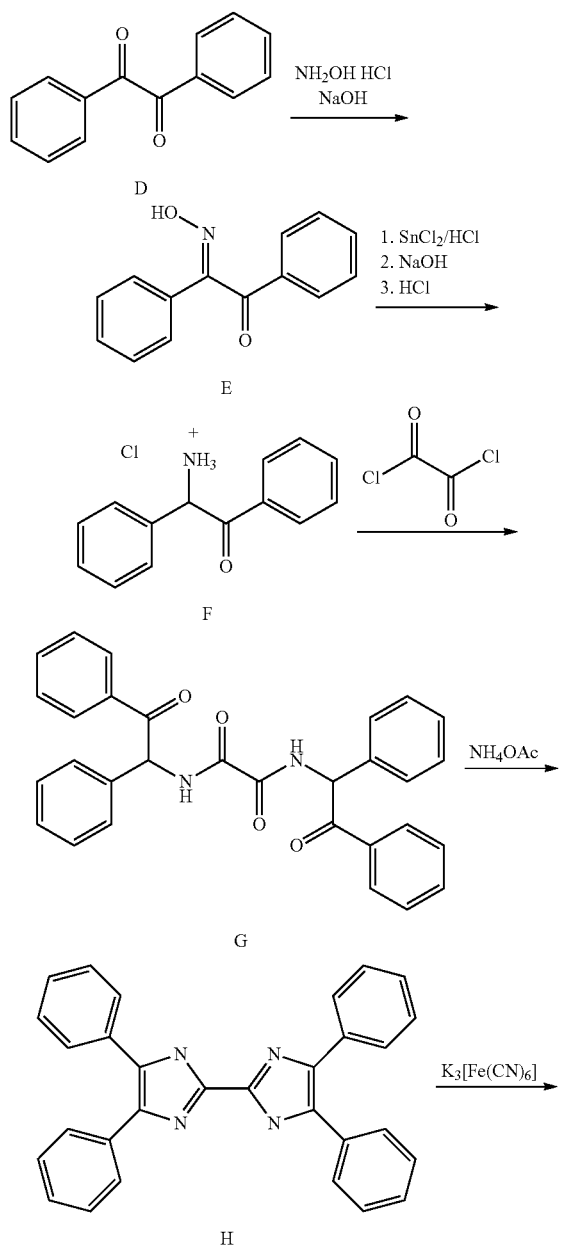

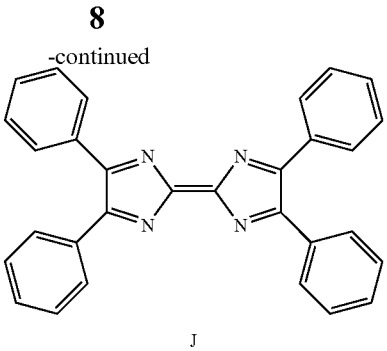

20 g (95 mmol) benzil D were added to 150 ml ethanol and were heated to boiling point. The solution was heated for ten minutes under reflux and was then cooled in an ice bath to 12° C. To the suspension obtained alternately and dropwise a solution of 6.6 g (95 mmol) hydroxylamine hydrochloride in 15 ml distilled water and 10 g (250 mmol) sodium hydroxide in 15 ml distilled water were added, wherein the internal temperature was kept under 15° C. After about 1.5 hours the addition was completed. The reaction mixture was left over night. It was then diluted with distilled water to a total volume of 600 ml, and non-converted benzil was filtrated by a filter. After acidifying the filtrate with semi-concentrated hydrochloric acid, the turbid solution was left. The crystals obtained were filtrated, washed with water and dried in vacuum at a temperature of 50° C. After recrystallization using toluene 15.4 g of colourless crystals of 1 were obtained. Yield: 72%.

Melting point: 139° C.—$^1$H-NMR (250 MHz, DMSO-d$_6$): 12.47 (1H, s, OH): 7.93-7.40 (10H, m, Phenyl-H)—13C-NMR (250 MHz, DMSO-d$_6$): 192.5 (C=O); 154.6 (C=NOH); 137.4; 135.1; 134.8; 133.4; 132.0; 130.7; 130.5; 129.8; 129.7; 129.5; 128.7; 128.4.

8.2 g (36.4 mmol) benzil monooxim E were dissolved at room temperature in ethanol (60 ml). 42 g tin(II)chloride in 80 ml concentrated hydrochloric acid were added. The turbid solution was stilled for one hour and then filtrated. The filtrate was kept in a refrigerator at 5° C. over night. The crystals obtained were filtrated, washed with litter cooled ethanol and dried in vacuum. 9.4 g of colourless crystals were obtained. These crystals were dissolved in as less water as necessary for dissolution (about 35 ml) and were brought to pH 12 with a solution of sodium hydroxide. The slightly yellow solid obtained was filtrated utilizing a G4-Fritte and was washed there after four times with diethylether and then twice with dioxane, until no further solid was dissolved. The basic aqueous solution was extracted twice with each 200 ml diethylether. After combination of all ether phases these were washed with 200 ml of water and were dried with sodium sulphate. The desylamin was precipitated from the solution using dry hydrogen chloride. The colourless solid F obtained was filtrated and dried in vacuum at 50° C. 3.58 g were obtained. Yield: 40%.

$^1$HNMR (250 MHz, DMSO-d$_6$): 9.08 (3H, s, NH$_{3+}$); 8.05 (2H, dd, Phenyl-H); 7.64-7.34 (8H, m, Phenyl-H); 6.37 (1H, s, CH)—$^{13}$C-NMR (250 MHz, DMSO-d$_6$): 193.8 (C=O); 134.8; 133.6; 133.1; 130.0; 129.8; 129.7; 129.5; 129.4; 129.4; 129.3; 58.4 (CHNH$_{3+}$).

Under argon atmosphere 1.5 g (6.1 mmol) desylamin hydrochlorid F and 0.26 mol (3.0 mmol) oxalyl chloride were provided in 2.0 ml dry toluene and were heated to 50° C. 4 ml pyridine were added dropwise within two hours, subsequently it was heated for two hours under reflux. The solvent was removed utilizing a rotatory evaporator, and the brown solid obtained was washed several times with water. After drying the raw product in an exsiccator utilizing phosphorous pentoxid the solid was heated with ethanol. After heat filtration and drying in vacuum at 40° C. 1.1 g of a tan solid G were obtained. Yield: 77%.

450 mg (0.95 mmol) N,N-bis-(phenylphenylacyl)-oxamid G and 12 g dry ammonium acetate were added to 90 ml glacial acetic acid and heated (140° C. bath temperature). After a short time a clear solution was obtained, which was heated under reflux for additional four hours. After cooling the reaction mixture it was neutralized under ice cooling with semi-concentrated ammonia. The crystals obtained were filtrated and recrystallized from ethanol. 390 mg of colourless solid H were obtained. Yield: 94%.

Melting point: 332° C.—$^1$H-NMR (250 MHz, CDCl$_3$): 7.42-7.26 (m, Phenyl-H)—$^{13}$C-NMR (250 MHz, CDCl$_3$): 137.1; 133.5; 131.0; 128.4-127.8.

150 mg (0.45 mmol) K$_3$[Fe(CN)$_6$] in 4 ml 1N KOH aq. were added to a solution of 85 mg (0.2 mmol) H in 4 ml CHCl$_3$, and this two phase mixture was stirred intensively for several hours. Already after a few seconds the CHCl$_3$-phase took a red colour, whereas the aqueous phase cleared up. After completed reaction the CHCl$_3$-layer was separated, dried over sodium sulphate and concentrated. The dark red crystalline solid J obtained was suspended in a suitable mixture of, for example, CHCl$_3$ and hexane, and filtered under suspension.

Implementation of Doping

Among others, phthalocyanine complexes, for example of Zn (ZnPc), Cu (CuPc), Ni (NiPc) or other metals, can be used as p-dopable matrix materials, whereby the phthalocynanine ligand can also be substituted. Other metal complexes of naphthocyanines and porphyrines can also be used. Arylated or heteroarylated amines and/or benzidine derivatives that are substituted or non-substituted, for example TPD, α-NPD, TDATA, more particularly also spiro-bonded aryl canines such as, for example, spiro TTB can also be used a matrix material. More particularly, α-NPD and spiro TTB can be used as matrix material.

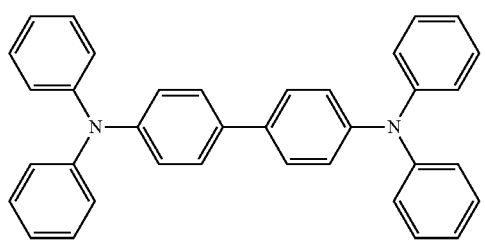

TPD

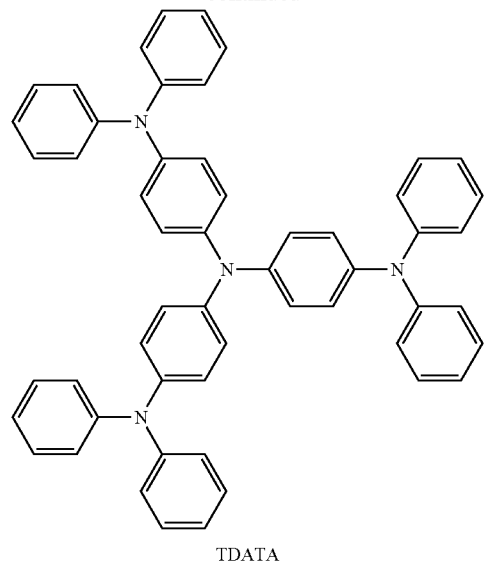

TDATA

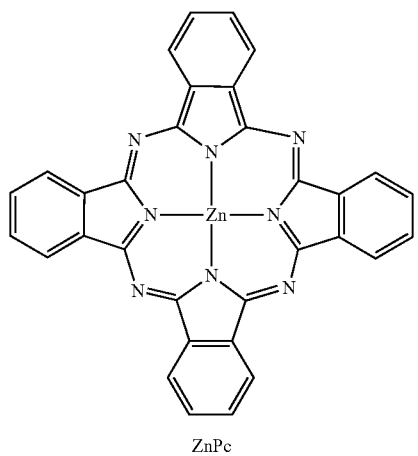

ZnPc

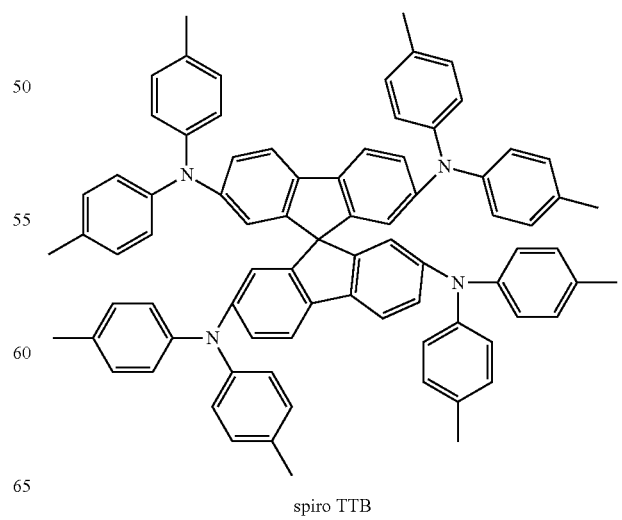

spiro TTB

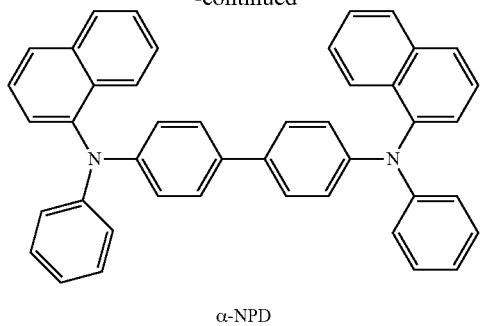

α-NPD

In addition to polyaromatic hydrocarbons, heteroaromates such as, in particular, imidazole derivatives, thiophene, thiazole derivatives, heterotriphenylenes but others too can also be used as matrix materials, possibly also dimer, oligomer or polymer heteroaromates. The heteroaromates are preferably substituted, more particularly aryl-substituted for example phenyl or naphthyl-substituted. They can also be present as Spiro compounds.

The said matrix materials can of course be used with each other or mixed with other materials within the context of the invention. Suitable other organic material materials that have semiconductor properties can also be used.

Doping Concentration

Preferably the dopant is present in a doping concentration of $\leq 1:1$ to the matrix molecule or the monomer unit of a polymer matrix molecule, preferably in a doping concentration or 1:2 of less, particularly preferably of 1:5 or less or 1:10 of less. The doping concentration can be in the range from 1:1 to 1:100,000, more particularly in the range from 1:5 to 10,000 or 1:10 to 1:1000, for example in the range from 1:10 to 1:100 or 1:25 to 1:50 without being limited thereto.

Implementation of Doping

Doping of the relevant matrix material with the compound to be used in accordance with the invention can take place by way of one or a combination of the following methods:
  Mixed evaporation in a vacuum with one source for the matrix material and one for the dopant.
  Sequential deposition of the matrix material and the p-dopant on a substrate with subsequent diffusing in of the dopant, particularly by way of thermal treatment.
  Doping of a matrix layer through a solution of p-dopant with subsequent evaporation of the solvent, particularly by way of thermal treatment.
  Surface doping of a matrix material layer by way of a superficially applied layer of dopant.
  Production of a solution of matrix molecules and dopant and subsequent production of a layer of this solution using conventional methods such as evaporation of the solvent or spin coating.

Other suitable methods of implementing doping can of course also be used. In this way p-doped layers of organic semiconductors can be produced that can be diversely used.

Semiconductor Layer

By way of the electron-deficient quinoid bisimidazoles used in accordance with the invention, semiconductor layers can be produced that may tend to be linear, such as, for example conductivity paths, contacts and suchlike. The quinoid bisimidazoles can hereby used as the p-dopant together with another compound that can act as matrix material, whereby the doping ratio can be 1:1 or less. The dopant used can, however, be present in greater proportions vis-à-vis the other compound/component so that the dopant compound ratio can be a ratio of 1:1, for example a ratio of $\geq 2:1$, $\geq 5:1$, $\geq 10:1$ or 20:1 or greater. The other component in each case can be one as can be used as matrix material in the case of producing doped layers, without being restricted thereto. If necessary the used dopant can also be essentially present in pure form, for example as a pure layer.

More particularly, the area containing, or largely Or completely comprising a dopant can be in electrical contact with an organic semiconductor material and/or an inorganic semiconductor material, for example it can be arranged on a substrate of this type.

Preferably said electron-deficient quinoid bisimidazoles are used as p-dopants in accordance with the invention, e.g. at a ratio of $\leq 1:1$ or $\leq 1:2$. By way of the electron-deficient compounds used as p-dopants in accordance with the invention, when using, for example. ZnPc, Spiro TTB or α-NPD as matrix, semiconductor layers with conductivities at room temperature of $10^{-5}$ S/cm or more can be achieved. When using phthalocyanine zinc (ZOO as the matrix, in the example of embodiment a conductivity of greater than $10^{-5}$ S/cm was achieved, The conductivity of undoped phthalocyanine zinc on the other hand is max. $10^{-10}$ S/cm.

It is self-evident that the layer or the structure with the dopants can each contain one or more different electron-deficient quinoid bisimidazoles of this type.

Electronic Structural Element

Using the described compound to produce p-doped organic semiconductor materials, which can in particular be arranged in the form of layers or electrical conductivity paths, a number of electronic components or devices containing these can be produced with a p-doped organic semiconductor layer. In the sense of the invention the term "electronic structural elements" also includes optoelectronic structural elements. By way of the described compounds the electronic properties of an electronically functional area of the component, such as it electrical conductivity, light-emitting properties or suchlike can be beneficially modified. Thus, the conductivity of the doped layers can be improved and/or improvement of the charge carrier injection of contact into the doped layer can be achieved.

The invention more particularly comprises organic light-emitting diodes (OLED), organic solar cells, field effect transistors, organic diodes, especially those with a high rectification ratio such as $10^3$-$10^7$, preferably $10^4$-$107$ or $10^5$-$10^7$, and organic field effect transistors than can be produced by means of the imidazole derivatives.

In the electronic component a p-doped layer may be present on the basis of an organic matrix material, for example in the following layer structures, whereby preferably the base material or matrix materials of the individual layers are each organic:
  p-i-n: p-doped semiconductor—intrinsically semiconducting layer—n-doped semiconductor,
  n-i-p: n-doped semiconductor—intrinsically semiconducting layer—p-doped semiconductor.

The contact materials are here hole-injecting, whereby on the p-side for example a layer or a contact of ITO or Au can be provided or electron-injecting whereby on the n-side layer or contact of ITO, Al or Au can b provided.

In the above structures the i-layer can be omitted it required, whereby layer sequences with p-n or n-p transitions can be obtained.

The use of the described compounds is not, however, restricted to the examples of embodiment set out above, and more particularly the layer structures can be supplemented/modified by the introduction of additional suitable layers. In particular, OLEDs with such layer sequences, especially with p-i-n or with a structure inverse thereto can be built up with the described compounds With the aid of the described p-dopants organic diodes of the type metal—intrinsic semiconductor—p-doped semiconductor (m-i-n) or also of the p-i-n type can in particular be produced, for example on the basis of phthalocyanine zinc. These diodes exhibit a rectification ratio (rectification ratio related to the current flow in the throughflow direction compared to the current flow in the blocking direction of the component) of $10^5$ and more. In addition, using the dopants in accordance with the invention electronic components with p-n transitions can be produced, whereby for the p and n-doped side the same semiconductor material is used in each case (home-p-n transition) and whereby for the p-doped semiconductor material a described imidazole derivative is used.

In accordance with the invention the imidazole derivatives can also be used in layer, conductivity paths, point contacts or such like, if these predominate over another component, for example as an injection layer in pure or essentially pure form.

Further objectives and advantages of the present invention are now clearly explained by way of the following example, which should only be considered as illustrative and not limiting for the scope of the invention.

Example of Embodiment of Doping by Way of a Quinoid Bisimidazole

An electron-deficient quinoid bisimidazole is provided as a dopant, purified through gradient sublimation in a high vacuum at least once.

The presented dopant is evaporated at the same time as the matrix material. In accordance with the example of embodiment the matrix material is phthalocyanine zinc or Spiro TTB. The p-dopant and the matrix material can be evaporated in such a way that the layer deposited on a substrate in a vacuum evaporation installation exhibits a molar doping ratio of p-dopant to matrix material of 1:10.

The layer of organic semiconductor material doped with the p-dopant is applied to an ITO layer (indium tin oxide) which is arranged on a glass substrate. Alter applying the p-doped organic semiconductor layer a metal cathode is applied, for example by vacuum evaporation of a suitable metal in order to produce an organic light diode. The organic light diode can of course also have a so-called inverted layer structure whereby the layer sequence is: glass substrate—metal cathode—p-doped organic layer—transparent conducting cover layer (for example ITO). Depending on the application further layers can of course be provided between the individually named layers.

Example 1

The quinoid bisimidazole derivative C was used for doping ZnPc and Spiro TTB as matrix material. Doped layers with a doping ratio of dopant:matrix material of 1:10 were produced by mixed evaporation of the matrix and dopant. The measured conductivities were $7.9\times10^{-5}$ S/cm in ZnPc and $4.6\times10^{-7}$ S/cm in spiro TTB.

Example 2

The quinoid bisimidazole derivative C was used for doping ZnPc as matrix material. Doped layers with a doping ratio of dopant:matrix material of 1:10 were produced by mixed evaporation of the matrix and the dopant. The measured conductivities were $1.0\times10^{-6}$ S/cm in ZnPc.

The features of the invention disclosed in the above description and in the claims can be essential both individually as well as in any combination for implementing the invention in its various forms of embodiment.

The invention claimed is:

1. An electronic or optoelectronic structural element comprising at least one organic matrix compound, and a p-dopant, wherein the p-dopant is an imidazole derivative represented by one of the following formulae:

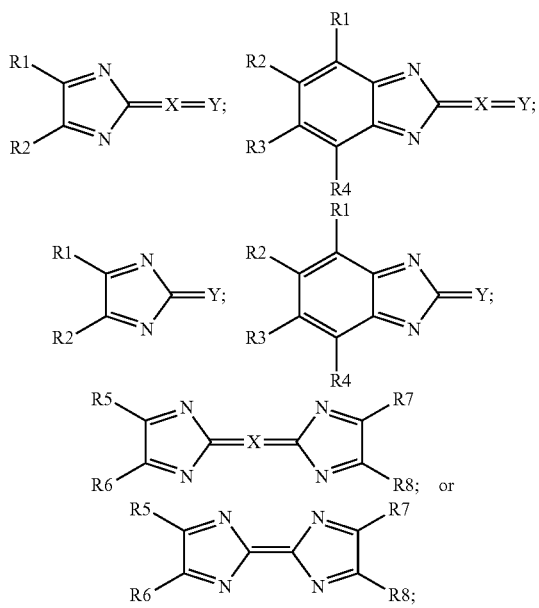

wherein X is selected from the group consisting of substituted and non-substituted conjugated double-bond systems, substituted and non-substituted quinoid aromatic ring systems, substituted and non-substituted quinoid anellated aromatic ring systems, substituted and non-substituted quinoid heteroaromatic ring systems, and substituted and non-substituted quinoid anellated heteroaromatic ring systems;

Y is selected from the group consisting of 2-indandione derivatives, $C(CN)_2$, NCN, O, 2-cyclopentadiene derivatives, 2-cyclopentenedione derivatives, $C(CF_3)_2$, $C(CN)$aryl, $C(CN)$oligoaryl, $C(CN)$heteroaryl, $C(CF_3)$aryl, $C(CF_3)$oligoaryl, $C(CF_3)$heteroaryl, N-heteroaryl, N-oligoaryl, acceptor-substituted aryl, and acceptor-substituted heteroaryl;

$R_1$-$R_8$ are independently selected from the group consisting of hydrogen, substituted and unsubstituted aryls, substituted and unsubstituted heteroaryls, substituted and substituted conjugated hydrocarbon chains with alternating C—C single and double bonds, halogen, cyano, pseudohalogen, nitro, halogenated or perhalogenated alkyls, carboxylic acids and derivatives thereof, and sulphonic acids and derivatives thereof; wherein at least one of $R_1$-$R_8$ is not hydrogen, or wherein two adjacent $R_1$-$R_8$ are elements of an aromatic ring system anellated to the imidazole ring; and wherein the p-dopant forms a dopant layer arranged on the matrix compound, or wherein the p-dopant and matrix compound form a p-doped layer having a concentration of the p-dopant to the matrix compound of less than 1:2 or more than 2:1.

2. The electronic or optoelectronic structural element according to claim 1, wherein X is selected from the group consisting of substituted and non-substituted quinoid aryls, substituted and non-substituted quinoid heteroaryls, and substituted and non-substituted conjugated hydrocarbon chains with alternating C—C single and double bonds.

3. The electronic or optoelectronic structural element according to claim 1, wherein the aromatic ring system anellated to the imidazole ring is substituted.

4. The electronic or optoelectronic structural element according to claim 1, comprising an electronically functional area, wherein the electronically active area comprises at least one of the imidazole derivatives.

5. The electronic or optoelectronic structural element in accordance with claim 4, wherein the electronically active area comprises the organic matrix compound and the p-dopant.

6. The electronic or optoelectronic structural element in accordance with claim 4, wherein the element is arranged as an organic light-emitting diode, a photovoltaic cell, an organic solar cell, an organic diode, or an organic field effect transistor.

* * * * *

UNITED STATES PATENT AND TRADEMARK OFFICE
CERTIFICATE OF CORRECTION

PATENT NO.         : 8,460,581 B2
APPLICATION NO.    : 12/599487
DATED              : June 11, 2013
INVENTOR(S)        : Horst Hartmann et al.

Page 1 of 1

It is certified that error appears in the above-identified patent and that said Letters Patent is hereby corrected as shown below:

In the Specifications:

At column 14, line 11, delete the "," after "compound".

At column 14, line 52, before "N-heteroaryl," insert --N-aryl--.

At column 14, line 58, after "and" delete "substituted" and insert --unsubstituted--.

Signed and Sealed this
Twenty-third Day of July, 2013

Teresa Stanek Rea
*Acting Director of the United States Patent and Trademark Office*